(12) United States Patent
Huppert et al.

(10) Patent No.: US 7,056,344 B2
(45) Date of Patent: Jun. 6, 2006

(54) OSSEOUS ANCHORING DEVICE FOR A PROSTHESIS

(75) Inventors: Jean Huppert, L'Etrat (FR); Marc Ameil, Reims (FR)

(73) Assignee: LDR Medical, Rosieres Pres Troyes (FR)

( * ) Notice: Subject to any disclaimer, the term of this patent is extended or adjusted under 35 U.S.C. 154(b) by 0 days.

(21) Appl. No.: 10/494,418

(22) PCT Filed: Nov. 6, 2002

(86) PCT No.: PCT/IB02/04642

§ 371 (c)(1),
(2), (4) Date: Jul. 22, 2004

(87) PCT Pub. No.: WO03/039400

PCT Pub. Date: May 15, 2003

(65) Prior Publication Data

US 2005/0065611 A1 Mar. 24, 2005

(30) Foreign Application Priority Data

Nov. 6, 2001 (FR) .................................. 01 14352

(51) Int. Cl.
*A61F 2/44* (2006.01)
(52) U.S. Cl. .................. 623/17.16; 623/17.11
(58) Field of Classification Search ... 623/17.11–17.16
See application file for complete search history.

(56) References Cited

U.S. PATENT DOCUMENTS

| 5,197,986 A | * | 3/1993 | Mikhail .................... 623/20.18 |
| 5,314,477 A | * | 5/1994 | Marnay .................... 623/17.15 |
| 5,358,526 A | * | 10/1994 | Tornier ..................... 623/19.14 |
| 5,401,269 A | * | 3/1995 | Buttner-Janz et al. ... 623/17.15 |
| 6,045,552 A | * | 4/2000 | Zucherman et al. ......... 606/61 |
| 6,344,057 B1 | * | 2/2002 | Rabbe et al. ............. 623/17.11 |
| 6,506,216 B1 | * | 1/2003 | McCue et al. ........... 623/20.34 |

FOREIGN PATENT DOCUMENTS

| FR | 2 659 226 A | 9/1991 |
| FR | 2 724 108 A | 3/1996 |
| WO | 99 56675 A | 11/1999 |

* cited by examiner

Primary Examiner—Thomas Barrett

(57) ABSTRACT

The present invention relates to an osseous anchoring device intended to maintain a prosthesis or an implant in position, and in particular an anchoring device for an intervertebral prosthesis. The anchoring device for a prosthesis (1), or an implant, is intended to be anchored in a prepared osseous surface (310, 321). It comprises at least one protruding element extending beyond the prosthesis, this protruding element being able to be positioned relative to the prosthesis in a plurality of positions thus making it possible to choose a position adapted to the case to be treated or to the chosen mode of inserting the prosthesis or the anchoring device.

10 Claims, 2 Drawing Sheets

OSSEOUS ANCHORING DEVICE FOR A PROSTHESIS

FIELD OF INVENTION

The present invention relates to an osseous anchoring device intended to maintain a prosthesis or implant in position, and in particular an intervertebral prosthesis.

BACKGROUND OF THE INVENTION

When an internal prosthesis bears on an osseous body or is inserted between several osseous bodies, the position of this prosthesis is often maintained in place by reliefs or irregularities of protruding form on one face of this prosthesis and acting as anchor in the surface of this osseous body.

In the case of intervertebral prostheses, in particular functionally replacing an intervertebral disc, this maintenance can be ensured in several ways. One possibility consists of providing pins extending beyond the surface of the prosthesis, these pins being encrusted, or impacted, in the surface of the vertebral disc, under the effect of the pressure exerted by the vertebrae surrounding the prosthesis.

The length of these impacting pins in nonetheless limited by the fact that the two vertebrae must be sufficiently separated to enable insertion of the prostheses and pins in the space thus obtained.

For obtaining greater anchoring depth, it is known from patent FR 2 659 226 how to use a prosthesis with one or several projections fixed in winged form, extending beyond the plates in contact with the vertebrae and oriented along a plane parallel to the sagittal plane of the rachis. The surgeon then begins by boring a trench in the surface of the vertebral disc opening into one of the sides of the body of the vertebra. This trench is made using a bone chisel or osteotome, and opens towards the outside in a direction corresponding to the direction in which the prosthesis and its winglet will be inserted.

Because of the position of the winglets parallel to the sagittal plane, and given that the prosthesis does not have a rotary shape and must be oriented in a precise angular position around the rachis axis, the prosthesis must therefore be inserted according, to a path allowing median access during the intervention, therefore usually an anterior path.

OBJECTS OF AND BRIEF DESCRIPTION OF THE INVENTION

The aim of the present invention is thus to overcome the disadvantages of prior art by means of an osseous anchoring device that makes it possible to set the same shape prosthesis from different accesses, for example lateral access, antero-lateral access or postero-lateral access.

This aim is achieved with an anchoring device for a prosthesis, or an implant, intended to be anchored in an osseous surface by impacting or by insertion in a housing prepared in this osseous surface, characterized in that it comprises at least one protruding element extending beyond this prosthesis, this protruding element being able to be positioned relative to the prosthesis in a plurality of positions thus making it possible to choose a position adapted to the case to be treated or the setting method chosen.

According to one feature, the protruding element is a winglet carried by and attached to a closely plane bearing face of the prosthesis, this winglet having an elongated shape that is disposed in a plane non-parallel to this bearing face.

According to a further feature, the prosthesis is an intervertebral prosthesis having at least one attached winglet, an intended to be anchored in the vertebral plate of at least one vertebra, the winglet being able to be positioned in a plurality of angular positions around an that is substantially closely perpendicular to the bearing face of the prosthesis or to the vertebral plate, the plurality of angular positions being defined by a plurality of co-operating means prepared in the bearing face of the prosthesis and co-operating with the complementary means on then winglet.

According to a further feature, the winglet is maintained in an angular position corresponding to at least one shape irregularity carried by the winglet and adapted to cooperate with the complementary shape on the prosthesis, or corresponding to a shape irregularity carried by the bearing face of the prosthesis and co-operating with the complementary shape on the winglet, or by shape irregularities carried by the winglet and by the bearing face and co-operating with each other.

According to a further feature, the winglet has a set of holes (preferably drilled holes) disposed along the plane of the winglet, fitted around a pin integral with the bearing face of the prosthesis, at least one of the two extremities of the winglet having a protruding part for fitting into a housing prepared in the bearing face of the prosthesis and thus maintaining the angular position of the winglet.

According to a further feature, the drilled hole(s) is located in the central part or, at one extremity of the winglet, this drilling and the pin being truncated in shape, with complementary tapering relative to each other, with angles sufficiently small to produce a certain maintenance in position of the winglet on the pin.

According to a further feature, the winglet has at least one its thickness, enabling the two opposite faces of the winglet to communicate.

According to a further feature, the winglet has shape irregularities on the surface of at least one of its faces, able to limit the risks of the winglet sliding in contact with the osseous matter.

According to a further feature, the shape irregularities are indentations formed on the crest of the winglet and/or on its lateral faces.

According to a further feature, the co-operating means are holes disposed on the bearing face of the prosthesis and the complementary means of the winglet are lugs extending beyond its face in contact with the prosthesis.

According to a further feature, the co-operating means are lugs extending beyond the bearing face of the prosthesis and the complementary means of the winglet are holes disposed in its face in contact with the prosthesis.

BRIEF DESCRIPTION OF THE DRAWING

The invention, together with its characteristics and advantages, will become clearer by reading the description below, in reference to the attached drawings in which.

DETAILED DESCRIPTION OF THE INVENTION

The present description refers to an anchoring device according to the invention applied to an inter-vertebral disc prothesis of a functional type, meaning that it allows relative movement of the two vertebrae.

Although the invention is described here for the case of such a prothesis, it must be evident that the anchoring device according to the invention can also be applied to other types of devices, for example nonfunctional such as, for example, an arthrodesic thoracic cage or a tumorous cage. In the present description, the term "prosthesis" must therefore be understood as being able to be applied equally well to a prosthesis as to an implant.

The anchoring device according to the invention can also be used for maintaining other types of prostheses, used for other reasons and in other regions of the body, when they comprise a part bearing against an osseous surface. The device according to the invention can also be combined with other anchoring devices, such as osseous anchoring pins or screws.

In the case (not shown) of an implant constituted of a tumorous cage, the device to be anchored, hereinafter called "the prosthesis" comprises a fixed structure intended to replace a vertebra or a part of a vertebra, when the existing vertebra has deteriorated, in particular after 5 ablation of a tumour.

Figure 1:
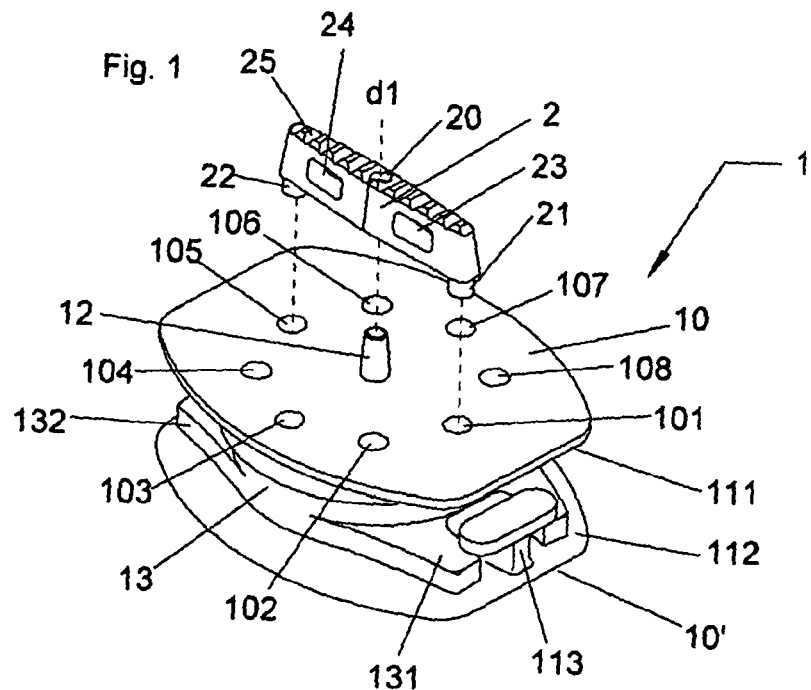
FIG. 1 shows a view in perspective, before positioning the winglet, of a disc prosthesis comprising an anchoring device according to an embodiment of the invention with a symmetrical winglet with apertures and allowing four angular positions.

In an embodiment shown in FIG. 1, a functional prothesis 1 for an intervertebral disc receives an anchoring device according to the invention.

The prosthesis comprises two plates 111, 112, surrounding a replacement disc, referred to herein as a nucleus, 13 with two curved sides, preferably with curvatures of different radii but oriented in the same direction. The plates 111, 112 bear in a complementary way on the two sides of the nucleus, the difference in curvature allowing lateral displacement of the nucleus when the two plates are inclined relative to each other. Around its periphery, the nucleus has two pairs 131, 132 of arms, each surrounding a pillar 101, 102 integral with one of the plates. This pillar has an upper part wider than the opening of the arms of the nucleus, and co-operates with the latter to limit lateral and vertical movement of the nucleus, thus preventing lifting of the nucleus when the plates are inclined.

Figure 3:
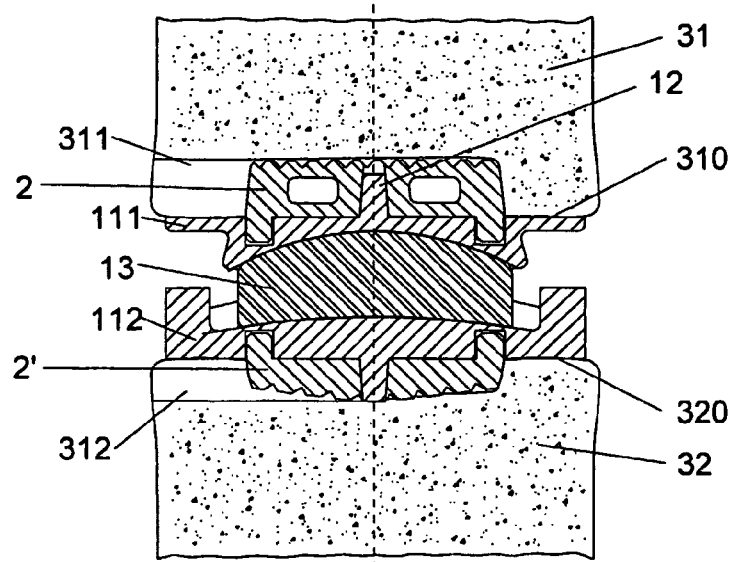
FIG. 3 shows a lateral cross section of a prosthesis in position between two vertebrae after setting by lateral access, this prosthesis comprising two anchoring devices according to the invention, one of them is an embodiment wherein the winglet does not have any apertures.

Each of the plates 111, 112 has an external face 10, 10' respectively, called a bearing face, with a substantially plane surface. Once in place between two contiguous vertebrae 31, 32 as shown in FIG. 3, each plate of the prosthesis bears against the part of each of the vertebrae opposite the other vertebra, that is to say against the vertebral plate 310, 320.

On the prosthesis receiving the anchoring device according to the invention, the external surface of the plate has at least one pin 12, preferably central, elongated along a direction perpendicular to this surface. A winglet 2, with elongated shape disposed in a plane non-parallel to the surface of the bearing face 10, and for example perpendicular to this surface, is fitted around this pin 12. This winglet comprises a hole 20 on one of its edges, this hole surrounding the pin 12 and co-operating with the latter to prevent any movement of the winglet 2 in translation in a plane parallel to the bearing surface 10. Advantageously, the hole 20 of the winglet and the pin 12 that it receives have closely complementary truncated shapes. These shapes thus have a sufficiently small angle of taper so that their interlock maintains the winglet on the pin, in particular during the phases of manipulation and setting of the prosthesis. Preferably, the bearing face comprises a pin 12 in its central region, and the hole 20 of the winglet is located in its central part. It is thus possible to notatably position said winglet on the pin in a plurality of angular positions on the bearing face and around said pin 12 as an axis. The prosthesis furthermore comprises a plurality of co-operating means that define the angular position by co-operating with the complementary means carried by the winglet.

In another embodiment (not shown), the winglet hole 20 is situated close to one of the winglet extremities or in any position on the bearing surface of the winglet.

The co-operating means are, for example, apertures disposed in the bearing face 10 of the prosthesis. The complementary means of the winglet 2 are then one or several protruding parts carried by the winglet on one of its extremities, or on both extremities, on the face opposite the bearing face 10 of the prosthesis.

In the embodiment shown here these housings are round holes 101 to 108 disposed on the bearing face of the prosthesis, and these protruding parts are lugs 21, 22 that are complementary to the holes 101 and are carried by the two extremities of the winglet. In certain angular positions of the winglet fitted on the bearing face pin, these lugs 21, 22 are inserted into the holes disposed in this same bearing face. These holes 101–108 then co-operate with the lugs of the winglet to maintain the angular position of the winglet around the pin 12, for example when inserting the prosthesis.

In an embodiment variant (not shown), the co-operating means are protruding parts, for example lugs, carried by the bearing face of the prosthesis. The complementary means are then housings, for example disposed, prepared in the winglet face in contact with the prosthesis. In this variant, it should be noted that the lugs carried by the prosthesis and not used by the winglet also combine to maintain the prosthesis in position, by impacting on the vertebral disc under the effect of the pressure of the vertebrae.

Figure 4:
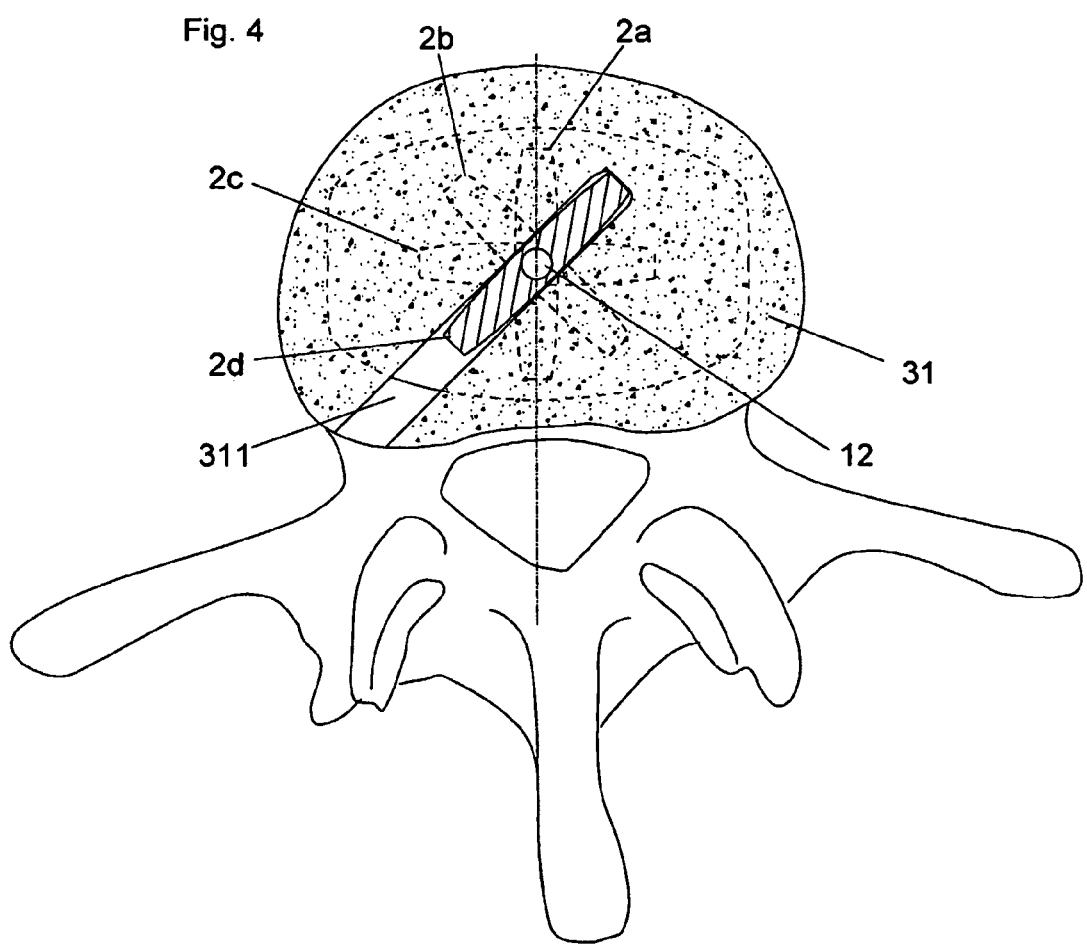
FIG. 4 shows a transversal cross section of a vertebra in which a prosthesis is anchored comprising an anchoring device according to the invention, after setting by postero-lateral access, in an embodiment with a symmetrical winglet without apertures and allowing four angular positions.

In an embodiment shown in FIG. 1, the upper plate 111 of the prosthesis 1 comprises on its bearing face 10 a group of eight holes distributed around the same radius circle around the pin 12 and having angular intervals of 45°. By inserting the lugs of the winglet 2 into any pair of two diametrically opposite holes, it is thus possible to position this winglet in any one of the angular positions defined by these hole couples. In an embodiment shown in FIG. 1, the eight holes allow four different angular positions if the winglet is symmetrical around the pin, meaning 0°, 45°, 90° and 135°, or eight positions if the winglet is not symmetrical. If one of these hole pairs corresponds to the sagittal plane, these four positions (2a, 2b, 2c, 2d, in FIG. 4) of the winglet make it possible to use the same winglet with the same prosthesis for insertion by median access, antero-lateral access, lateral access or postero-lateral access.

Figures 2A, 2B:
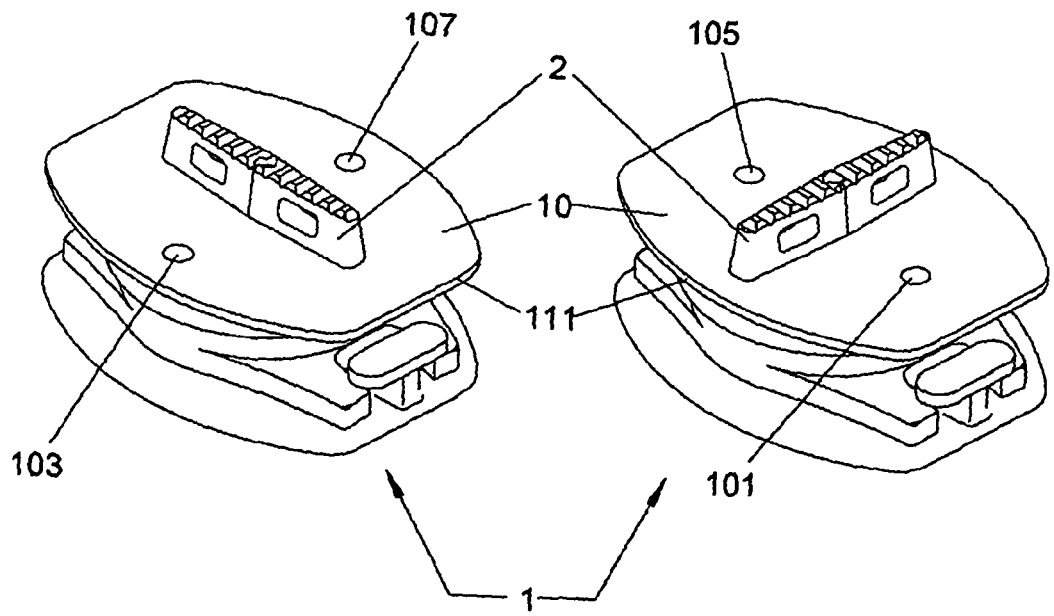
FIGS. 2a and 2b show a view in perspective of a disc prosthesis comprising an anchoring device according to an embodiment of the invention with a symmetrical winglet with recesses and allowing two angular positions, the winglet being positioned for setting by lateral access or by median access respectively.

In the embodiment shown in FIGS. 2a and 2b, the anchoring device according to the invention comprises four holes 101, 103, 105, 107, and makes it possible to set the winglet in two angular positions. FIG. 2a thus shows the winglet mounted for setting by median access, and FIG. 2b shows the winglet mounted for setting by lateral access.

It should be understood that the invention also makes it possible to supply a one and only prosthesis with its anchoring device for several different setting methods, which thus reduces the number of versions to be manufactured or kept in stock.

Before inserting the prosthesis, a housing 311, 321, in trench form is hollowed out in the surface of each of the vertebral plates 310, 320 respectively. This housing is, for example, made in such a way that it only opens onto a single side 311, FIG. 4, and is oriented along the same side as the setting provided for the prosthesis.

When setting, the winglet can thus slide into this trench from the vertebral plate side to enable the prosthesis to arrive in its intended position without having to separate the vertebrae too much.

According to the applications, the winglet can have one or several, apertures 23, 24, that enable the two opposite faces to communicate. These recesses can, for example, be filled with osseous matter reconstituted material excavated from the two sides of the trench 311. This filling thus allows the winglet to maintain maintenance in position of the winglet to be consolidated in the vertebral plate.

The winglet 2 can also have shape irregularities on one or several of its sides, for example notches or indentations 25, which make it possible to limit the risks of sliding in the trench 311 by attaching to the walls of said trench. On one or several of its sides, the winglet 2 can also comprise an anti-slip surface obtained, for example, by direct molding, by surface marking, or by coating. In particular, such a surface state can be produced in hot textured titanium.

It must be evident to those skilled in the art that the present invention allows embodiments under many other specific forms without extending beyond the field of application of the invention as claimed. Consequently, the present embodiments must be considered as illustration only, but can be modified in the domain defined by the range of the attached claims, and the invention must not be limited solely to the details given hereabove.

The invention claimed is:

1. An anchoring device for an intervertebral prosthesis adapted to be anchored in the vertebral endplate of at least one vertebra, said device comprising at least one protruding element that is attached to a bearing face of the intervertebral prosthesis, wherein the protruding element is adapted to be positioned in a plurality of angular positions around an axis that is substantially perpendicular to the bearing face of the prosthesis, the plurality of angular positions controlled by a plurality of cooperating structures disposed in the bearing face of the prosthesis in operative relationship to complementary structure(s) on the protruding element.

2. The anchoring device according to claim 1, wherein said protruding element comprises a flattened, elongated winglet, wherein said winglet is disposed in a plane that is not parallel to said bearing face.

3. The anchoring device according to claim 1, wherein the protruding element is maintained in an angular position relative to said bearing face, with respect to at least one shape irregularity carried by the protruding element and that is adapted to cooperate with the complementary shape on the prosthesis.

4. The anchoring device according to claim 1 wherein said protruding element has two extremities and at least one hole disposed along the plane of the protruding element that is adapted to cooperate with a pin that is substantially integral with the bearing face of the prosthesis, and wherein at least one of the two extremities of the protruding element has a protruding part adapted to fit into a housing disposed in the bearing face of the prosthesis to maintain the angular position of the protruding element.

5. The anchoring device according to claim 4 wherein said hole(s) is located in a central part of the protruding element, said hole(s) and a pin extending from said bearing face adapted to cooperate with said hole(s) are truncated in shape, with complementary tapering angles relative to each other, wherein said angles are sufficiently small so as to enable maintenance in position of the protruding element relative to the prosthesis.

6. The anchoring device according to claim 1 wherein the protruding element has at least one aperture through its thickness, that is adapted to enable two opposing faces of the protruding element to communicate with each other.

7. The anchoring device according to claim 1 wherein the protruding element has at least one shape irregularity disposed on the surface of a face that is adapted to contact an osseous surface and to thereby deter the protruding element from sliding in relationship to the osseous matter.

8. The anchoring device according to claim 7, wherein said shape irregularity(ies) comprise indentations disposed on a crest of the protruding element or on at least one of its lateral faces.

9. The anchoring device according to claim 1, wherein the co-operating structures are holes disposed on the bearing face of the prosthesis and the complementary structure(s) disposed on the protruding element are lugs that are adapted to extend beyond a face of said protruding element that is adapted to be proximate to said bearing face.

10. The anchoring device according to claim 1, wherein the co-operating structures are lugs adapted to extend beyond the bearing face of the prosthesis and the complementary structure of the protruding element are holes disposed in its face in contact with the prosthesis.

* * * * *